(12) United States Patent
Matta

(10) Patent No.: US 7,824,353 B2
(45) Date of Patent: Nov. 2, 2010

(54) SURGICAL SUPPORT FOR FEMUR

(76) Inventor: Joel M. Matta, 30031 Ahern Ave., Union City, CA (US) 94587-1234

( * ) Notice: Subject to any disclaimer, the term of this patent is extended or adjusted under 35 U.S.C. 154(b) by 589 days.

(21) Appl. No.: 10/930,809

(22) Filed: Sep. 1, 2004

(65) Prior Publication Data

US 2006/0064103 A1   Mar. 23, 2006

(51) Int. Cl.
*A61F 5/00* (2006.01)
*A61B 1/32* (2006.01)
(52) U.S. Cl. .......................... 602/35; 600/201
(58) Field of Classification Search ......... 128/845–846, 128/869, 882, 877–879; 248/302–304, 692; 5/624, 648; 600/206, 208, 201, 215, 210; 294/26, 19.1, 82.1; 606/276, 246
See application file for complete search history.

(56) References Cited

U.S. PATENT DOCUMENTS

| | | | | |
|---|---|---|---|---|
| 4,143,652 A | * | 3/1979 | Meier et al. | 600/203 |
| 4,373,709 A | * | 2/1983 | Whitt | 5/650 |
| 4,428,571 A | * | 1/1984 | Sugarman | 5/648 |
| 6,012,456 A | * | 1/2000 | Schuerch | 128/869 |
| 6,315,718 B1 | * | 11/2001 | Sharratt | 600/228 |

OTHER PUBLICATIONS

Definition of unitary and continuous.*

* cited by examiner

*Primary Examiner*—Patricia M Bianco
*Assistant Examiner*—Tarla R Patel
(74) *Attorney, Agent, or Firm*—Theodore J. Bielen, Jr.

(57) ABSTRACT

A surgical support for a femur utilizing a shaft having a proximal portion and a distal portion. The shaft lies along an axis which is coincident with a first plane. A hook connects to the shaft through an intermediate portion and lies in a second plane which intersects the first plane. The hook includes a flattened portion for support of the femur.

5 Claims, 3 Drawing Sheets

SURGICAL SUPPORT FOR FEMUR

BACKGROUND OF THE INVENTION

The present invention relates to a novel and useful surgical support for a femur.

Recent advances in surgery focus on minimally invasive techniques, which generally, reduce the size of the incision and eliminate the detachment or severing of muscles.

In this regard, minimally invasive hip replacement surgery utilizes entry at the anterior of the patient's leg. By following such approach, the surgeon may accomplish a hip replacement by utilizing a four inch incision rather than a ten inch incision in the prior technique. Also, muscles within the leg are not damaged, resulting in fast recovery of the patient and eliminating muscle detachment during the post operative time.

Anterior approach hip replacement techniques still require access to the acetabulum which must be cleared prior to the insertion of the artificial femur head. In addition, proper manipulation and positioning of the femur is essential in carrying out the anterior approach hip replacement surgery.

A support for a femur during surgical techniques such as hip replacement would be a notable advance in the medical field.

BRIEF SUMMARY OF THE INVENTION

In accordance with the present invention a novel and useful support for a femur during surgical procedures is herein provided.

The support of the present invention utilizes a shaft possessing a proximal portion and a distal portion. At least a part of the shaft lies along an axis which coincides with a first plane. The shaft may terminate in an end fitting which allows the shaft to be mounted on a jack associated with a surgical table.

A hook is also employed in the present invention and lies in a second plane. The first and second planes intersect one another. That is to say, the hook is connected to the shaft by an intermediate portion and is angulated to properly position the femur and allow the surgeon to effect hip replacement without the femur obstructing access to the acetabulum of the hip. Hooks may be oppositely angled relative to the shaft to accommodate the right or left femur of a patient.

A base member is also employed for positioning the shaft relative to the surgical table. The base member may be fastened to the table or separately supported. In certain aspects of the present invention the base member may take the form of a bracket having a plurality of openings. Each opening in the bracket is capable of accommodating a portion of the shaft, namely the end portion of the shaft in most cases. The base member may be connected to a jack associated with the surgical table.

It may be apparent that a novel and useful support for a femur bone during a surgical procedure has been hereinabove described.

It is therefore an object of the present invention to provide a support for a femur bone during a surgical procedure which adequately supports the femur and provides the surgeon with access to anatomical portions of the hip in order to effect artificial hip replacement.

Another object of the present invention is to provide a support for a femur bone during a surgical procedure which is compatible with surgical tables used in surgery.

Another object of the present invention is to provide a support for a femur bone during a surgical procedure which allows the practicing of non-invasive hip replacement surgery and permits fast recovery of patients having such surgery.

A further object of the present invention is to provide a support for a femur bone during a surgical procedure which supports the femur and which is adjustable in conjunction with a bracket as well as other components found on conventional surgical tables.

Another object of the present invention is to provide a support for a femur bone during a surgical procedure which is easily engageable with the femur and disengagable when not required during the surgical procedure.

The invention possesses other objects and advantages especially as concerns particular characteristics and features thereof which will become apparent as the specification continues.

For a better understanding of the invention reference is made to the following detailed description of the preferred embodiments thereof which should be referenced to the prior described drawings.

DETAILED DESCRIPTION OF THE PREFERRED EMBODIMENTS OF THE INVENTION

Various aspects of the present invention will evolve from the following detailed description of the preferred embodiments thereof which should be referenced to the hereinbefore delineated drawings.

Figure 1:
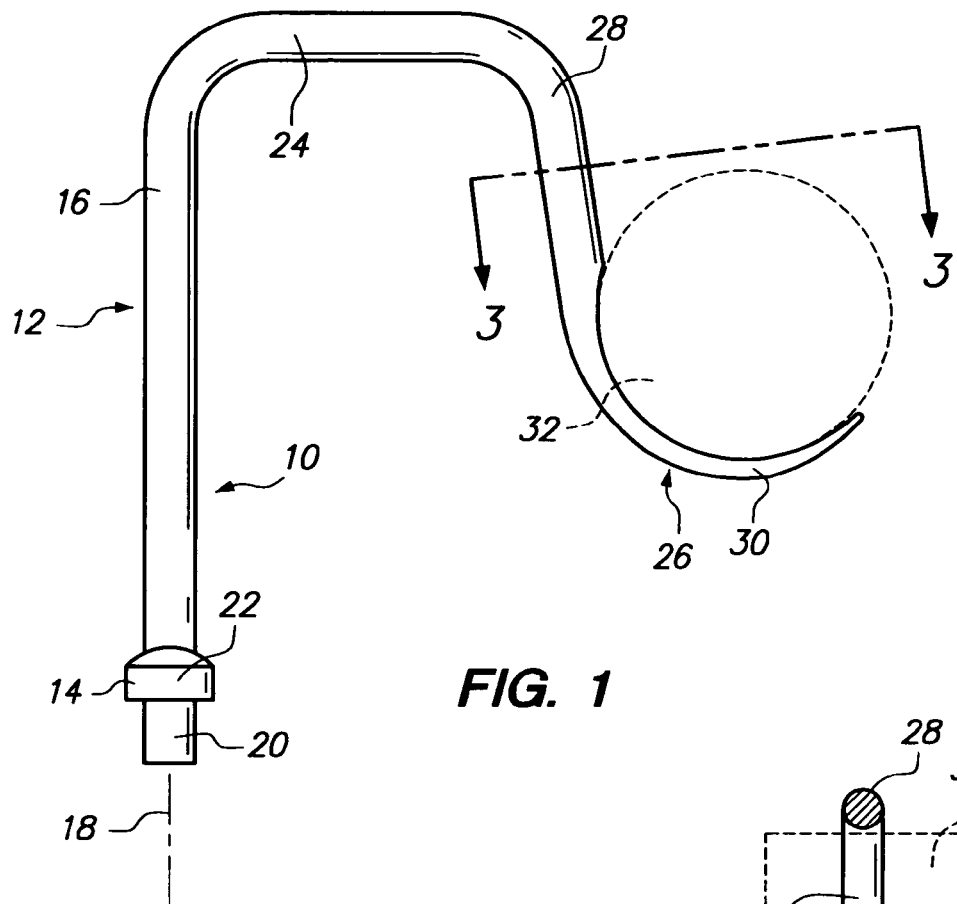
FIG. 1 is a side elevational view of the support of the present invention showing a femur in phantom.
Figure 3:
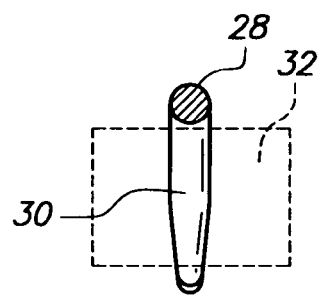
FIG. 3 is a sectional view taken along line 3-3 of FIG. 1.
Figure 2:
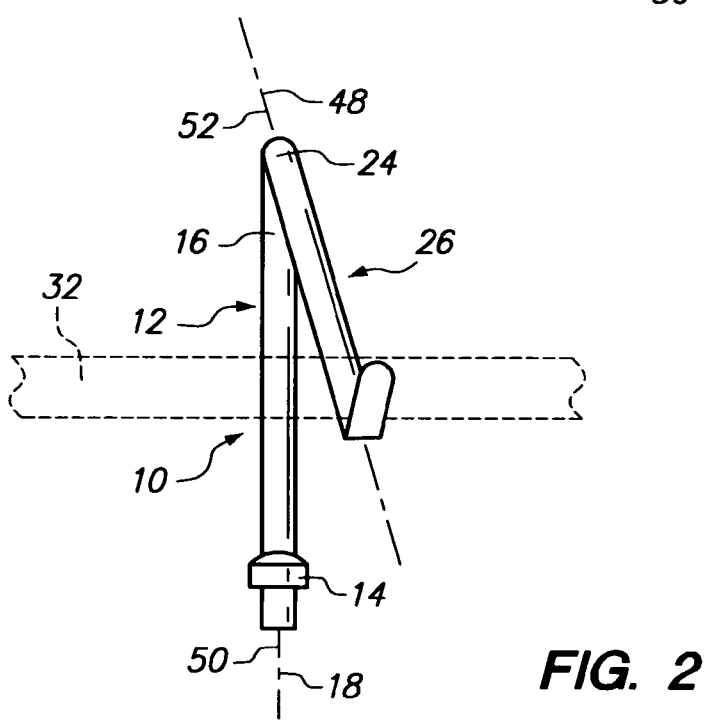
FIG. 2 is a front elevational view of a left handed support for a left leg of the present invention with a femur depicted in phantom.

The preferred embodiment of the invention is depicted as a whole in the drawings by reference character 10. With reference to FIGS. 1-3, support 10 includes as one of its elements a shaft 12. Shaft 12 possesses a proximal portion 14 and a distal portion 16. Shaft 12, or at least a portion of shaft 12, lies along axis 18. Shaft 12 may be formed of any rigid material such as metal, composites, and the like. Proximal portion 14 of shaft 12 includes a rectangular solid end 20 and a cap 22, the purpose of which will be discussed hereinafter.

The distal portion 16 of shaft 12 leads to an intermediate or spanning portion 24 and is formed of the same material as shaft 12. Intermediate portion 24 terminates in a rounded hook 26 a left-handed version. It should be realized that hook 26 may be squared or otherwise angulated. Hook 26 is formed with a tubular end 28 and a flattened curved section 30. Femur 32 is depicted in FIGS. 1 and 2 as lying within the flattened portion 30 of hook 26. The shaft 12, intermediate portion 24, and hook 26 form a continuous or one-piece member.

Figure 4:
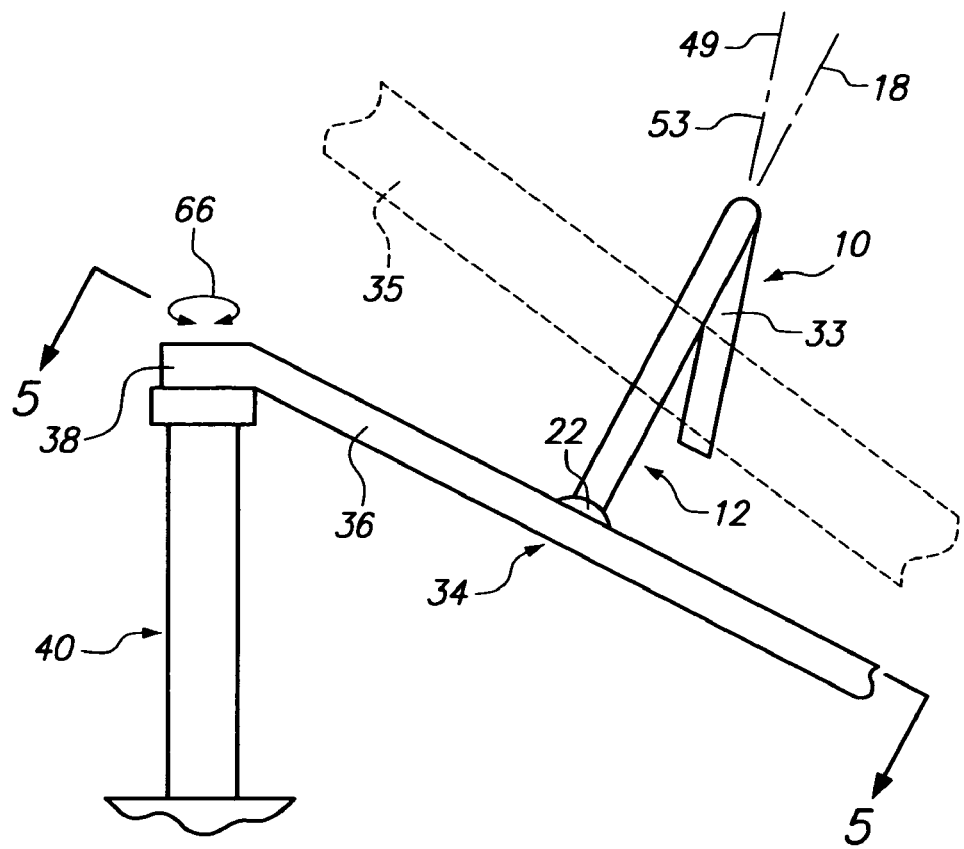
FIG. 4 is a rear elevational view of a right handed support for a right leg of the present invention located in a bracket connected to a jack, partially shown.
Figure 5:
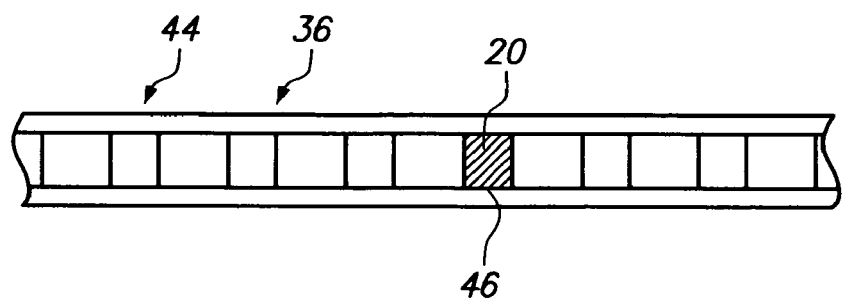
FIG. 5 is a partial sectional view taken along line 5-5 of FIG. 4.

Referring now to FIG. 4, it may be observed that support 10, having a right-handed hook 33 holding left femur 35 is also provided with a base member 34. Base member 34 may take the form of a bracket 36 which includes and end portion 38 that connects to a jack 40 which is part of a conventional surgical table 42 shown in FIG. 6. With reference to FIG. 5, it may be apparent that bracket 36 includes a plurality of opening 44 each of which is intended to fit rectangular solid end 20 of support shaft 12. Cap 22 serves to limit the penetration of rectangular solid end 20 of shaft 12 into any one of the plurality of openings 44 of bracket 46. It should be noted that end 20 of bracket 12 lies in opening 46 within bracket 36. With reference to FIGS. 2 and 4, it should be seen that end 48 of hook 26 and the end of hook 33 lie along axes 48 and 49, respectively, which are not parallel or coincident with axis 18. In fact, axis 18 lies in a plane 50, while axes 48 and 49 lie in planes 52 and 53. Planes 50 and 52, and planes 50 and 53, intersect one another. Such angular orientation between hooks 26 or 33 and shaft 12 provides the proper angle to left femur 32 and right femur 35, respectively, which are supported by hooks 26 or 33 during hip surgery.

Figure 6:
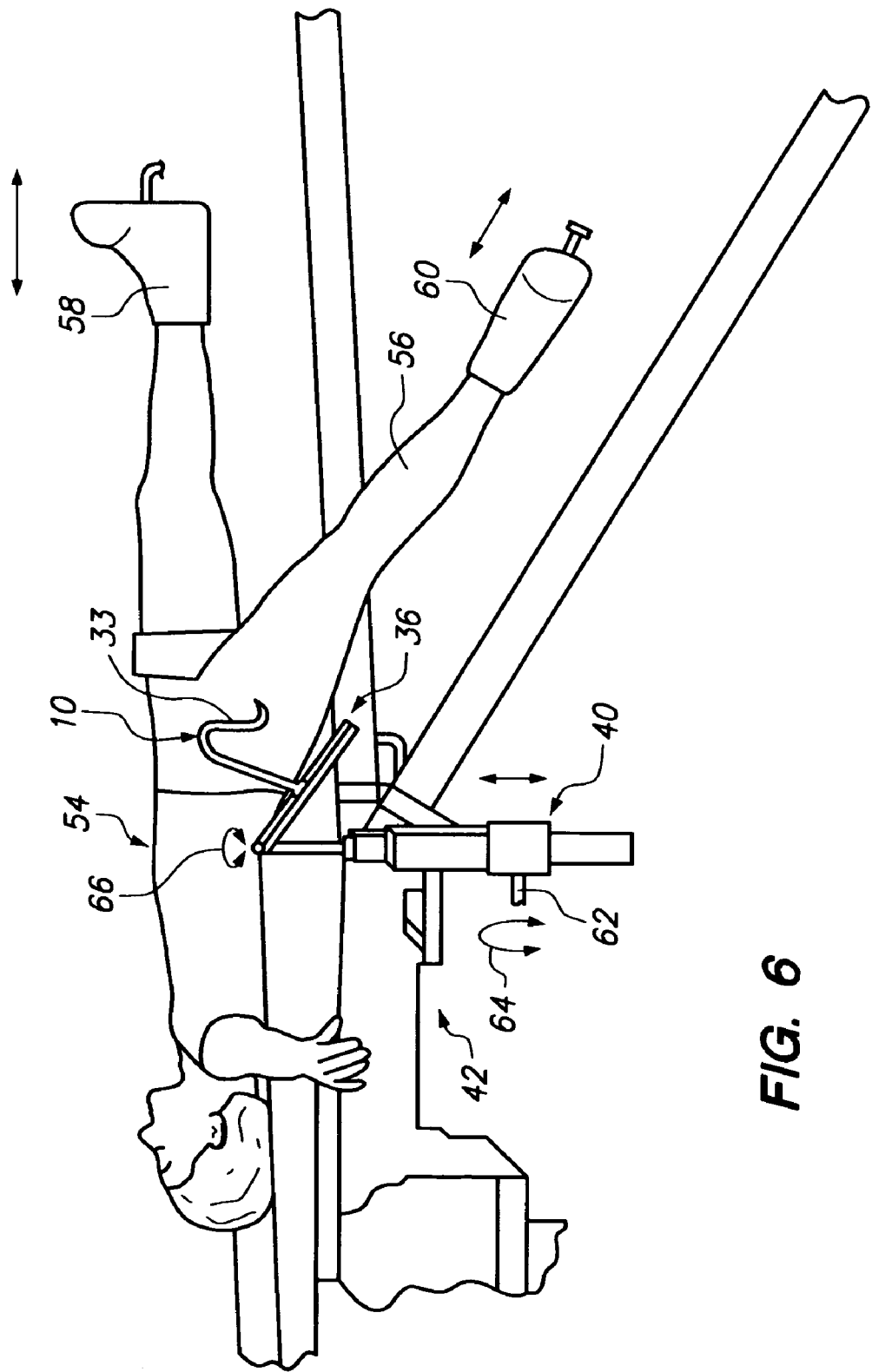
FIG. 6 is a schematic view indicating the positioning of the support of the present invention using a right-handed hook with a conventional surgical table partially depicted, with a patient in the supine position prior to hip replacement surgery.

With reference to FIG. 6, anesthetized patient 54 is shown in place on surgical table 42 a position ready for anterior approach hip surgery on the hip associated with right leg 56. Traction boots 58 and 60 are employed and are used to provide traction through a mechanism of table 42, not shown completely in FIG. 6. In this regard, a surgical table known as the PRO fx manufactured by Orthopedic Systems, Inc. of Union City, Calif. would suffice in this regard. Surgical table jack 40 is able to raise and lower support 10 connected to bracket 36. The raising and lowering of jack 40 takes place through a rotatable shaft 62, partially shown, the motion of which is indicated by directional arrow 64. Bracket 36 is also capable of rotating relative to jack 40 such that the surgeon performing non-invasive hip surgery possesses complete control of the positioning of support 10 relative to femur 35, shown in phantom on FIGS. 1-4, within right leg 56.

In operation, the user places support 10 on base member 34 in the form of bracket 36 in the preferred embodiment. Such mounting is accomplished by the placement of end 20 of shaft 12 of support 10 within any of the plurality of openings 44 of bracket 36. At the proper time after an incision is made in patient 54, FIG. 6, hook 26 or 33 enters the wound at the hip region of patient 54 and supports right femur 32 or left femur 35, respectively. Typical jack 40, in combination with support 10, is able to properly angle and support left femur 35 such that the surgeon is capable of gaining unrestricted access to the acetabulum and other portions of the hip in order to accomplish an artificial hip replacement for a patient 54, FIG. 4. When support 10 is no longer needed, support 10, including hook 26 or 33, is swung from the wound in patient 54 and moved outwardly by the rotation of bracket 36 relative to typical jack 40, directional arrow 66. Support 10 may then be removed or left in this position as surgery progresses and is finished.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A device intended for directly contacting and supporting a femur bone within a wound of a subject during a surgical procedure, comprising:
   a. a shaft, said shaft possessing a proximal portion and distal portion, at least a portion of said shaft lying along a first axis which coincides with a first plane;
   b. a hook, said hook including an end, said hook end lying along a second axis which coincides with a second plane, the first and second planes intersecting one another, said hook further possessing a free tip configured and intended to enter the wound of the subject, said hook further intended for directly contacting the femur;
   c. an intermediate portion connecting said shaft and said hook, said intermediate portion extending laterally from said shaft axis, said shaft, said hook end, said hook free tip, and said shaft, hook, and intermediate portion forming a one-piece member without articulation, said intermediate portion and said hook lying apart from said axis of said shaft and a base member; said base member including a bracket having a plurality of openings spaced from each other along said bracket, each of said openings accommodate a portion of said shaft.

2. The support of claim 1 in which said shaft, said hook end, said hook free tip, and intermediate portion one-piece member without articulation comprises a one-piece tubular member without articulation.

3. The support of claim 1 in which said one-piece member without articulation comprises a rigid body.

4. The support of claim 1 in which said hook free tip includes a flattened portion.

5. The support of claim 1 in which said shaft includes an end portion configured to fit in any of said spaced openings of said bracket.

* * * * *